US011045404B2

(12) United States Patent
Su et al.

(10) Patent No.: US 11,045,404 B2
(45) Date of Patent: Jun. 29, 2021

(54) THICKENING CLEANSING COMPOSITIONS AND APPLICATIONS AND METHODS OF PREPARATION THEREOF

(71) Applicants: Sino Lion USA LLC, Florham Park, NJ (US); Nanjing Huashi New Material Co., Ltd., Nanjing (CN)

(72) Inventors: Evelyn Su, East Hanover, NJ (US); Huiyu Wang, Madison, NJ (US); Jing Sha, Madison, NJ (US)

(73) Assignees: Sino Lion USA, Florham Park, NJ (US); Nanjing Huashi New Material Co., Ltd., Nanjing (CN)

(*) Notice: Subject to any disclaimer, the term of this patent is extended or adjusted under 35 U.S.C. 154(b) by 0 days.

(21) Appl. No.: 16/062,454

(22) PCT Filed: Dec. 14, 2016

(86) PCT No.: PCT/US2016/066545
§ 371 (c)(1),
(2) Date: Jun. 14, 2018

(87) PCT Pub. No.: WO2017/106276
PCT Pub. Date: Jun. 22, 2017

(65) Prior Publication Data
US 2019/0282480 A1 Sep. 19, 2019

Related U.S. Application Data

(60) Provisional application No. 62/267,275, filed on Dec. 14, 2015.

(51) Int. Cl.
*A61K 8/00* (2006.01)
*A61K 8/44* (2006.01)
*A61K 8/46* (2006.01)
*A61K 8/49* (2006.01)
*A61Q 5/02* (2006.01)
*A61Q 19/10* (2006.01)
*C11D 1/94* (2006.01)
*C11D 3/33* (2006.01)
*C11D 1/88* (2006.01)
*C11D 3/30* (2006.01)
*C11D 3/43* (2006.01)
*C11D 1/83* (2006.01)
*C11D 17/00* (2006.01)
*C11D 1/90* (2006.01)
*C11D 1/92* (2006.01)
*C11D 1/10* (2006.01)

(52) U.S. Cl.
CPC ............... *A61K 8/44* (2013.01); *A61K 8/442* (2013.01); *A61K 8/466* (2013.01); *A61K 8/4946* (2013.01); *A61Q 5/02* (2013.01); *A61Q 19/10* (2013.01); *C11D 1/83* (2013.01); *C11D 1/88* (2013.01); *C11D 1/94* (2013.01); *C11D 3/30* (2013.01); *C11D 3/33* (2013.01); *C11D 3/43* (2013.01); *C11D 17/003* (2013.01); *A61K 2800/20* (2013.01); *A61K 2800/805* (2013.01); *C11D 1/10* (2013.01); *C11D 1/90* (2013.01); *C11D 1/92* (2013.01)

(58) Field of Classification Search
CPC ........................................................ A61K 8/44
See application file for complete search history.

(56) References Cited

U.S. PATENT DOCUMENTS

| 5,672,740 | A | 9/1997 | Subramanyam et al. | |
|---|---|---|---|---|
| 8,193,137 | B2 | 6/2012 | Kunieda et al. | |
| 2012/0157365 | A1 | 6/2012 | Fevola | |
| 2012/0208898 | A1 | 8/2012 | Dong et al. | |
| 2013/0101543 | A1* | 4/2013 | Tamareselvy | C08F 2/00 424/70.11 |
| 2014/0349902 | A1* | 11/2014 | Allef | A61K 8/361 510/119 |
| 2015/0141466 | A1 | 5/2015 | Klug et al. | |
| 2016/0200668 | A1 | 7/2016 | Wang et al. | |

FOREIGN PATENT DOCUMENTS

| CN | 1918258 A | 2/2007 |
|---|---|---|
| CN | 103435509 A | 12/2013 |
| CN | 104095764 A | 10/2014 |
| EP | 2612653 A1 | 7/2013 |
| EP | 2682161 B1 | 7/2016 |
| JP | 2000248300 A | 9/2000 |
| WO | 2009125367 A1 | 10/2009 |
| WO | 2012029514 A1 | 3/2012 |
| WO | 2015024385 A1 | 2/2015 |
| WO | 2016067853 A1 | 5/2016 |

OTHER PUBLICATIONS

Kaser, Heike: Naturkosmetische Rohstoffe, 3, Auflage (Verlag Frey, Linz, Osterreich, 2012), S. 338-340.
Datenblatt Plantapon SF, BASF.
Material Safety Data Sheet, Plantapon SF, Gracefruit Ltd., Oct. 10, 2014.
Greisbach, Ute, Serviing the natural trend, Household and Personal Care Today, Nr. 2, 2010, S. 57-59.
(CHEMICALLAND21.COM) Sodium Cocoyl Glutamate (Mar. 18, 2006), (retrieved from the internet on Feb. 7, 2017) <URL: http://www.chemicalland21.com/specialtychem/perchem/SODIUM%20GLUTAMATE.htm> 2 pages.

\* cited by examiner (Continued)

Primary Examiner — Necholus Ogden, Jr.
(74) Attorney, Agent, or Firm — Fox Rothschild LLP

(57) ABSTRACT

The present invention discloses self-thickening compositions comprising one or more N-acyl acidic amino acid and/or a salts thereof and one or more amphoteric surfactant, methods of preparation thereof, and their applications in cosmetics and personal care, home care and other fields with excellent thickening performance and easy-to-use applicability, in particular in cleansing formulations to improve performance such as foam quality and mildness.

19 Claims, No Drawings

THICKENING CLEANSING COMPOSITIONS AND APPLICATIONS AND METHODS OF PREPARATION THEREOF

CROSS-REFERENCE TO RELATED APPLICATIONS

This application is a U.S. national phase application of International Application No. PCT/US2016/066545, filed Dec. 14, 2016, which in turn claims priority under 35 U.S.C. § 119(e) to U.S. Provisional Application No. 62/267,275, filed Dec. 14, 2015, the disclosure of both of which is incorporated herein by reference in their entireties.

FIELD OF THE INVENTION

The present invention relates to self-thickening surfactant compositions, preparation methods thereof, and their applications in cosmetics and personal care, home care, industrial and institutional cleaning, oil fields, etc.

BACKGROUND OF THE INVENTION

The cosmetic and personal care industry has witnessed increasing popularity and importance of "sulfate-free" personal care cleansing products containing environmentally friendly, sustainable and mild surfactants. Amino acid-based surfactants are considered to be "greener", milder and more sustainable than sulfate surfactants. Among the amino acid based surfactants, N-acyl acidic amino acids and salts thereof, such as acyl glutamate and their sodium, potassium, and TEA salts, have been known for their exceptional mildness when used in personal cleansing formulations as compared to other conventional surfactants such as the prevalent alkylether sulfates or the like. The acyl glutamate surfactants are among the most green and sustainable surfactants that are commercially available and practical for use in the cosmetic and personal care formulations, due to the fact that acyl glutamate surfactants are made completely from natural, renewable and sustainable feedstock, i.e., fatty acids and glutamic acid and/or their salts. Fatty acids are made from coconut oil, palm oil or palm kernel oil, while glutamic acid and the salt thereof are made from fermentation. Acyl glutamate surfactants have been known for their excellent safety, biodegradability, sustainability as well as their outstanding performance in terms of foam volume, foam quality, hard-water tolerance, mildness, ease of rinsing, moisturizing, reduction of skin adsorption of alkylether sulfate, soft skin after-feel, color retention for dyed hair, etc., so they have the most potential to become the next generation surfactants to totally replace the current prevailing surfactant types, e.g., alkylether sulfates such as sodium laureth sulfate (SLES).

However, a great long-existing challenge has prevented the widespread use of the acyl glutamate surfactants in personal cleansing products, that is, the extreme difficulty to thicken the surfactant systems containing acyl glutamate for any cleansing formulations. Among the four popular categories of amino acid based surfactants, i.e., acyl glycinate, acyl sarcosinate, acyl alaninate, and acyl glutamate, acyl glutamate is the most difficult to thicken due to its unique molecular structure containing a relatively large head with two water soluble carboxylic acid groups. To overcome this thickening difficulty associated with acyl glutamate surfactant, various special polymers have been attempted to thicken the surfactant systems containing acyl glutamate. Nevertheless, the polymer strategy only achieved very limited success, while most conventional thickening methods including many conventional polymers and salt addition do not work at all. Even among the limited success with the polymer strategy, new problems emerge with the addition of sufficient amount of a polymer thickener in personal care cleansing compositions containing the acyl glutamate, which often causes undesirable sensory attributes, poor foaming, sliminess during rinsing, as well as added cost.

Chinese Patent Application Publication No. CN104095764A has disclosed a self-thickening composition of viscoelastic micelle system comprised of cocoamidopropyl hydroxysultaine and sodium lauroyl sarcosinate. However, this patent application did not address any thickening issue of the acyl glutamate surfactant, which is much more difficult to thicken than acyl sarcosinate. U.S. Pat. No. 8,193,137 has revealed a thickening composition containing N-acyl acidic amino acid and/or a salt thereof, an amphipathic substance, an inorganic salt, and water as essential components. Nevertheless, this invention only achieved a relatively low viscosity range for "sulfate-free" surfactant systems even with a very high concentration of acyl glutamate, such as sodium cocoyl glutamate (20-26%) and a very high level of the amphipathic substance (5-14%), which would result in significant added costs. In addition, applications of the thickening compositions have also been rather limited, mainly in conventional shampoo and shower gel compositions containing sodium laureth sulfate as the primary surfactant, instead of a sulfate-free cleansing formulation containing mainly the green, renewable and sustainable acyl glutamate as the main surfactant.

Therefore, it is highly desirable to develop a cost-effective non-polymer thickening solution to the thickening challenge of acyl glutamate-containing cleansing compositions, especially where the acyl glutamate is used as a primary surfactant.

SUMMARY OF THE INVENTION

The present invention provides self-thickening compositions to overcome the afore-mentioned challenges on the acyl glutamate surfactant systems.

In one aspect, the present invention provides highly efficient and cost-effective non-polymer thickening solutions to aqueous sulfate-free cleansing formulations with acyl glutamate as the primary surfactant. The afore-mentioned self-thickening surfactant composition can be obtained by the use of one or more N-acyl acidic amino acid and/or a salt thereof as component A and one or more amphoteric surfactant as component B, water as the medium as component C, and optionally one or more additives and other ingredients as component D, with a suitable weight percentage and weight ratio within a pH range of 4.0-7.0.

In another aspect, the present invention provides an easy-to-use and easy-to-thicken acyl glutamate surfactant blend and a non-polymer acyl glutamate thickener for use in any aqueous cleansing formulations which is self-thickening within a suitable pH range.

In another aspect, the present invention provides a method for producing the composition.

In another aspect, the present invention provides the use of the composition for any aqueous cleansing formulation including but not limited to personal care, home care, institutional and industrial cleaning, etc.

The present invention has discovered for the first time a highly efficient and cost effective self-thickening composition containing one or more acyl glutamate surfactant, one or more amphoteric surfactant, and water as the medium with optional one or more additives and/or other ingredients. The thickening composition of the present invention can be totally polymer-free, and the amphoteric surfactant is of the common kind which is widely used in personal care and easily available at reasonable cost. The thickening composition in the present invention has efficiently and cost-effectively resolved the thickening challenge of the acyl glutamate surfactant, which enables its widespread use in personal cleansing formulations.

The afore-mentioned thickening composition in the present invention can be used in personal care applications such as hair shampoos, facial cleansers, shower gels, liquid cleansers, baby shampoos, feminine wash, etc. The thickening composition in the present invention may also be used in treating or caring for skin and/or hair, as well as in home care such as hand dish detergents, carpet and fabric care or laundry detergents, or in institutional and industrial applications such as diary cleaners, or oil field applications and more.

Thus, without limitation the present invention can be illustrated with the following embodiments:

[1] A composition containing the following components:
A. one or more N-acyl acidic amino acid and/or a salt thereof;
B. one or more amphoteric surfactant;
C. optionally water;
D. optionally one or more other ingredients;
wherein component C (water) can be added separately and/or along with any of components A,B and/or D; and the composition has a pH in the range of about 4.0 to about 7.0 with a viscosity in the range of about 200 to about 100,000 mPa·s when mixed with water.

[2] A composition containing the following components:
A. one or more N-acyl acidic amino acid and/or a salt thereof;
B. one or more amphoteric surfactant;
C. water;
D. optionally one or more other ingredients
Wherein component C (water) can be added separately and/or along with any of components A, B and/or D, and the composition has a pH in the range of about 4.0 to about 7.0 with a viscosity in the range of about 200 to about 100,000 mPa·s.

[3] The composition of [1] and [2], wherein the N-acyl acidic amino acid of component A is selected from N-acyl glutamic acid, N-acyl aspartic acid and the like or a mixture thereof, and the salt thereof is selected from sodium, potassium, ammonium or triethanolamine (TEA) salt or a mixture thereof.

[4] The composition of any one of [1] to [3], wherein the acyl group of the acyl acidic amino acid derives from one or more fatty acids comprising a C8 to C22 carbon chain.

[5] The composition of [4], wherein the fatty acid is selected from the group consisting of caprylic acid, capric acid, lauric acid, myristic acid, palmitic acid, stearic acid, isostearic acid, oleic acid, linoleic acid, eicosanoid, behenic acid, coconut acid, palm fatty acid and hydrogenated beef tallow fatty acid, and mixtures thereof.

[6] The composition of any one of [3] to [5], wherein the N-acyl glutamic acid is selected from the group consisting of cocoyl glutamic acid, caprylyol glutamic acid, capryol glutamic acid, lauroyl glutamic acid, myristoyl glutamic acid, palmitoyl glutamic acid, and mixtures thereof; and wherein the salt is any one of cocoyl glutamate, caprylyol glutamate, capryol glutamate, lauroyl glutamate, myristoyl glutamate, palmitoyl glutamate salts, or a mixture thereof, comprising one or two counter cation selected from the group consisting of sodium, potassium, ammonium, trimethylamine, and mixtures thereof.

[7] The composition of any one of [1] to [6], wherein the amphoteric surfactant of component B is selected from one or more types of betaines, hydroxysultaines (also called "sulfobetaines" or "sultaines"), phosphobetaines, imidazoline amphoterics; amphoacetates, propionates, and mixtures thereof.

[8] The composition of any one of [1] to [7], wherein the amphoteric surfactant of component B is selected from the group consisting of cocoamidopropyl betaine, coco betaine, lauramidopropyl betaine, lauryl betaine, cocoamidopropyl hydroxysultaine, lauramidopropyl hydroxylsultaine, coco hydroxysultaine, lauryl hydroxylsultaine, sodium lauromphoacetate, sodium cocoamphoacetate, disodium lauroamphodiacetate, disodium cocoamphodiacetate, and mixtures thereof;

[9] The composition of any one of [1] to [8], wherein the optional one or more other ingredients as Component D are selected from anionic and/or nonionic surfactants, cationic and/or cationizable surfactants, fatty amines, conditioning agents, silicones, vegetable oils, synthetic oils, moisturizing agents, polymers, actives, vitamins, sunscreens, anti-dandruff agents, skin lighteners, plant extracts, chelating agents, salts, colorants, dyes, pH adjusters, fragrances, preservatives, and mixtures thereof.

[10] The composition of [9], wherein the anionic surfactants are selected from acyl glycinate, acyl sarconsinate, acyl ananinate, acylmethyl taurates, alkyl isothionates, alkylether carboxylate, alkylsulfosuccinates, fatty acid salt, alkyl sulfates, alkylether sulfates, and combinations thereof; the cationic surfactants are selected from quaternary surfactants such as cetrimonium halides, steartrimonium halides and mixtures thereof; and the cationizable surfactants are selected from fatty amines such as stearamidopropyl dimethylamine, stearamidopropyl diethylamine, behenamidopropyl dimethyamine, behenamidopropyl diethyamine and mixtures thereof; and the non-ionic surfactants are selected from alkylpolyglucosides, alkanolamids, alkoxylated triglycerides, amine oxides, sorbitan esters.

[11] The composition of any one of [1] to [10], wherein the weight percentage of component A in active content is 0.5-60%, preferably 1.0-50%; more preferably 2.0-40%; still more preferably 3.0-30%; further more preferably 3.5-20%; particularly more preferably 4.0-10.0%

[12] The composition of any one of [1] to [11], wherein the weight percentage of component B in active content is 0.5-60%, preferably 1.0-50%; more preferably 1.5-40%; still more preferably 2.0-30%; further more preferably 2.5-20%, particularly more preferably 3-10%;

[13] The composition of any one of [1] to [12], wherein the weight percentage of water as component C is 0.01-98%; preferably 10-95%; more preferably 15-90%; still more preferably 20-85%, further more preferably 30-80%, particularly more preferably 40-75%. In some other embodiments, the composition may be preferably in the more concentrated range of 0.01-50%.

[14] The composition of any one of [1] to [13], wherein the weight percentage of one or more optional other ingredients as component D is 0-20%, preferably 0.05-15%; more preferably 0.1-10%, still more preferably 0.2-8%; further more preferably 0.5-5%, particularly more preferably 1-3%;

[15] The composition of any one of [1] to [14], wherein the pH is within 4.0-7.0; preferably 4.5-6.5; more preferably 4.8-6.3; still more preferably 4.9-6.0; further more preferably 5.0-5.5; particularly more preferably 5.1-5.4;

[16] The composition of any one of [1] to [15], wherein the total weight percentage of component A and B is 1-100%, preferably 2-80%; more preferably 3-70%; still more preferably 4-60%; further more preferably 5-50%; particularly more preferably 5-20%;

[17] The composition of [1] and [2], wherein the weight percentage of component A is 0.5-60%; component B is 0.5-60%; water is 0.01-98% and component D is 0-20%;

[18] The composition of [1] and [2], wherein the weight ratio of component A to component B is within 95:5 to 5:95, preferably 10:1 to 1:10; more preferably 5:1 to 1:5, still more preferably 4:1 to 1:4, further more preferably 3:1 to 1:3, particularly more preferably 2:1 to 1:2;

[19] The composition of [1] and [2], wherein water is 0.01-75% to provide a concentrated surfactant blend of a self-thickening composition;

[20] A self-thickening composition comprising an N-acyl acid amino acid and/or salt thereof (component A) and an amphoteric surfactant (component B), the composition having a pH in the range of about 5.5 to about 12.0 with a viscosity suitable for ease of transporting and handling, wherein the viscosity of the composition will increase to a desired higher viscosity as needed when it is used in a formulation by dilution with water and adjustment of pH;

[21] A method for producing a composition according to any one of [1] to [19], comprising the steps of (a) mixing component A and component B in their suitable weight percentages along with optional component C and optional component D; (b) stirring the mixture with mild heating as needed until it becomes uniform, and (c) adjusting pH with an acid and/or a base until a desired viscosity is obtained.

[22] A method for producing the thickening composition of [20], comprising mixing component A and component B in a limited amount of water in a pH in the range of about 5.5 to about 12.0 until it becomes uniform;

[23] A method for producing a concentrated blend of the composition [19] by mixing component A and component B with 0.01-75% water in order to make the acyl glutamate surfactant blend with the desired active content;

[24] A composition as an acyl glutamate surfactant thickener, comprising one or more amphoteric surfactants as component B, optionally with water and/or component D, which can be used as a standalone acyl glutamate surfactant thickener to thicken acyl glutamate surfactant-containing compositions.

[25] A method for producing the afore-mentioned acyl glutamate thickener of [24] by mixing one or more amphoteric surfactants as component B, optionally with water and one or more component D; which can be used to thicken acyl glutamate surfactant-containing compositions;

[26] A cleansing composition comprising a composition of any one of [1] to [20] for use in cosmetic or personal care, home care, institutional and industrial, oil field.

[27] The cleansing composition of [26], wherein the cleansing composition is for cosmetic or personal care use.

[28] The cleansing composition of [26] or [27], wherein the cosmetic or personal care cleansing composition is selected from liquid cleansers, body washes, shower gels, hair shampoos, baby shampoos, and facial cleansers.

[29] The cleansing composition of [26], wherein the cleansing composition is for home care use.

[30] The cleansing composition of [26] or [29], wherein the home care cleansing composition is selected from liquid hand cleansers, liquid dish detergents, and liquid laundry detergents, fabric cleansers, carpet cleaners, and furniture cleaners.

[31] The cleansing composition of [26], wherein the cleansing composition is for institutional and industrial use.

[32] The cleansing composition of [26] or [31], wherein the institutional or industrial cleansing composition is selected from hand cleansers, diary cleaners, fabric cleaners, carpet cleaners, and furniture cleaners.

[33] The cleansing composition of [26], wherein the cleansing composition is for an application in an oil field.

These and other aspects or advantages of the present invention will become clear in the following detailed description, examples, and claims.

DETAILED DESCRIPTION OF THE INVENTION

Amino acid based surfactants (also called "amino acid surfactants") are a category of the greener, safer and milder surfactants well-suited for personal care and cosmetic applications due to their safety, mildness and sustainability compared to the currently prevailing surfactants of alkylether sulfates such as sodium laureth sulfate (SLES). Among the four major amino acid surfactants, namely acyl glycinates, acyl glutamates, acyl sarcosinates and acyl ananinates, acyl glutamates are the most sustainable and cost effective surfactants, which can practically become the next generation surfactants to replace the current prevalent surfactants of alkylether sulfates, such as SLES, for the very first time for the betterment of the mankind and the environment, given that the present invention has also resolved the thickening challenge of the acyl glutamates enabling their widespread use in any cleansing formulations.

The present invention has successfully achieved the goal of providing a highly efficient and cost-effective non-polymer thickening solution to the aqueous sulfate-free cleansing formulations with acyl glutamate as the primary surfactant. In particular, the thickening solution is accomplished by a self-thickening composition containing one or more N-acyl acidic amino acid and/or a salt thereof as component A, one or more amphoteric surfactants as component B, water medium as component C, and optionally one or more additives and/or other ingredients as component D, with a suitable weight percentage within a pH range of 4.0-7.0, resulting in a desirable high viscosity range at a suitable pH. The self-thickening composition can increase the viscosity by 5 to 5,000 fold or more up to a viscosity of about 100,000 mPa·s or higher within the pH range of 4.0-7.0 with a suitable total weight percentage of component A and B as well as a suitable weight ratio of component A to B.

N-acyl acidic amino acid and/or a salt thereof as component A in the present invention may be those obtained by the known method of Schotten-Baumann reaction of acidic amino acid and fatty acid halide. As the acidic amino acid for component A, glutamic acid, aspartic acid and the like, or a mixture thereof, can be used. They can be in any of the L form, D form or a DL form or a combination of two or more forms selected from these. Among the acidic amino acid, glutamic acid is preferred due to its superior stability and performance after acylation. The acyl glutamate and the salt thereof as component A can be expressed with a common Formula I as shown below:

Formula I

Wherein, R1=C5 to C21 alkyl group, with either straight carbon chain or branched, saturated or unsaturated with one or more double bond, derived from one single fatty acid or a mixture of two or more fatty acids; and each of M1 and M2 independently represents H, Na, K, NH4, triethylamine TEA, or the like. M1 and M2 can be either the same or different. Furthermore, the acyl glutamate and/or the salt thereof can be either in the high purity solid form or in liquid form of an aqueous solution, while the latter is more preferable due to ease of handling.

The acyl group can be derived from long chain fatty acids, including but not limited to C6-C22 saturated and/or unsaturated fatty acids, for example, caprylic acid, capric acid, lauric acid, myristic acid, palmitic acid, stearic acid, isostearic acid, oleic acid, linoleic acid, behenic acid, coconut fatty acid, palm fatty acid, hydrogenated beef tallow fatty acid, and the like may be used. Either one kind or a mixture of two or more of the above mentioned fatty acids may be used. Preferably, coconut fatty acid, lauric acid and myristic acid may be selected due to their superior performance in foaming and foaming quality as well as skin-feel.

The salt of component A, i.e., M1 or M2, is not in any way limited. For example, M1 or M2 can be alkali metals such as sodium, potassium and the like, alkaline earth metals such as calcium, magnesium and the like, organic amines such as ammonia, monoethanolamine, diethanolamine, triethanolamine and the like, and organic salts such as basic amino acids such as arginine, lysine and the like. Either one kind or a mixture of two or more of the above mentioned salts may be used. Preferably, alkali metal salts, organic amine salts and basic amino acids may be selected; and more preferably, sodium, potassium, triethnolamine and arginine may be used due to their easy availability and superiority in handling and performance.

The one or more amphoteric surfactants as component B in the present invention include, but are not limited to, betaines, hydroxysultaines (also called "sulfobetaines" or sultaines), phosphobetaines, imidazoline amphoterics; amphoacetates, propionates, and the like, which can be either in solid or liquid form, while the liquid form of aqueous solution preferred due to ease of handling. Either one kind or a mixture of two or more of the above-mentioned amphoteric surfactants may be used. The betaines, sultaines and phosphobetaines can be expressed with two common formulas to represent the two types, i.e., alkyl betaines in Formula II and alkylamido betaines in Formula III, as shown below:

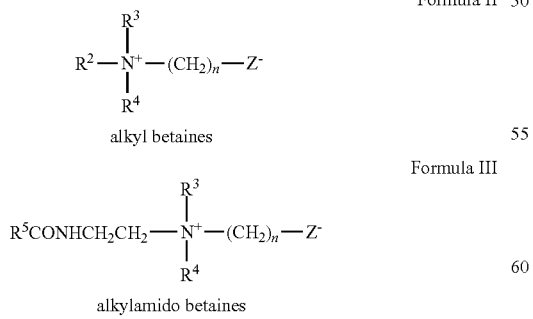

Formula II
alkyl betaines

Formula III
alkylamido betaines

Wherein, R2=C6 to C22 alkyl or alkenyl group, R3 and R4 are independently H or C1 to C4 alkyl, R3 and R4 can be the same or different, n=1 to 6, R5=C5 to C21 alkyl or alkenyl group. Z=—COO; —SO3, —CHOHCH2SO3, —HPO4; or —CHOHCH2OP(OH)O2. The alkyl betaines represented in Formula II are commonly made through condensation of an alkyl tertiary amine with a halogenated acid such as chloroacetic acid, chloroethyl sulfonic acid, chlorohydroxypropyl sulfonic acid, phosphoroxychloride, chlorohydroxyethyl phosphoric acid, etc. Typical examples are dimethylhexyl amine, dimethylcapryl amine; dimethyldecyl amine, dimethyllauryl amine, methylethyllauryl amine, dimethylcocoyl amine, dimethylmyristyl amine, dimethylcetyl amine, dimethylstearyl amine, methylhexylstearyl amine, dimethylloleyl amine, dimethylcetearyltallow amine, and their mixtures thereof.

Wherein R5 in Formula III includes, but not limited to, a straight or branched chain saturated C5-C21 alkyl group, or unsaturated C5-C21 alkenyl group, which is derived from long-chain fatty acids. The betaines represented in Formula III are typically prepared by first making an intermediate through a reaction of a fatty acid and a dimethylpropane diamine, then condensing such intermediate with a halogenated acid, such as chloroacetic acid, chloroethyl sulfonic acid, chlorohydroxypropyl sulfonic acid, phosphoroxychloride, chlorohydroxyethyl phosphoric acid, and industrial mixtures thereof. Typical fatty acids include, but not limited to, C6-C22 saturated fatty acid, benzoic acid, phenyl acetic acid, oleinic acid, linolic acid, linolenic acid, isocaprylic acid, isostearic acid, coconut acid, palm acid, soybean acid, erucic acid, etc., and preferably, C8-C22 fatty acid, and more preferably, C8-C18 fatty acid.

Typical betaines and hydroxylsultaines include, but not limited to, lauryl betaine, lauramidopropyl betaine, coco betaine, cocoamidopropyl betaine, lauryl hydroxysultaine, laurylamidopropyl hydroxysultaine, coco hydroxysultaine, cocoamidopropyl hydroxysultaine, lauryl phosphobetaine, cocoamidoethylhydroxyethyl phosphobetaines, etc.

The common formula for sodium alkyl amphoacetate can be expressed by Formula IV as follows:

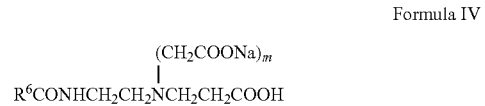

Formula IV while the general formula for alkyl imidazolines can be expressed by Formula V as follows:

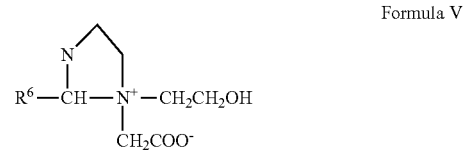

Formula V

Wherein, R6 in formula IV and formula V refers to a straight or branched chain saturated C7-C21 alkyl group, or a straight or branched chain mono-unsaturated or poly-unsaturated C7-C21 alkenyl group, which are derived from a long-chain fatty acid. In formula IV, m=1 or 2. The sodium alkyl amphoacetates are commonly prepared by first making an intermediate through a non-cyclization reaction of a long-chain fatty acid and hydroxyethyl ethylenediamine, and then reacting the intermediate with sodium chloroacetate. The alkyl imidazoline amphoteric surfactants are typically reaction products of a cyclic intermediate made through a cyclization reaction of a long-chain fatty acid and hydroxyethyl ethylenediamine, and then reacting the cyclic intermediate with sodium chloroacetate, and industrial mixtures thereof. Typical long-chain fatty acids include, but not limited to, C6-C22 saturated fatty acid, such as oleinic acid, linolic acid, linolenic acid, isocaprylic acid, isostearic acid, coconut acid, palm acid, soybean acid, and erucic acid, etc., and preferably, C8-C22 fatty acid, and more preferably, C8-C18 fatty acid.

Water as component C in the present invention is not limited in any way provided that it is of a purity level suitable for cleansing formulations. It can come from the media of component A or B or both, and it may also be added separately in addition to the amounts of water from the media of component A or B or both. In particular, de-ionized water, distilled water, purified water, well water, natural water, underground water, public water, hard water, soft water and the like can be used. One kind or a mixture of two or more of these kinds of water may be used. Preferably, de-ionized water or distilled water may be used due to the superior suitability for product preservation and hygiene for the application of the present invention.

The optional one or more other ingredients as component D in the present invention are not particularly limited, which include but not limited to one or more additional anionic and/or non-ionic surfactants, cationic compounds, including but not limited to cationic or cationizable surfactants, conditioning agents, moisturizing agents, polymers, silicones, actives, chelating agents, salts, fragrances, preservatives, etc. Some of these additives may have further thickening synergies with the self-thickening composition disclosed in this invention, in particular, cationic surfactants such as cetyltrimonium chloride, cetyltrimonium bromide, stearyltrimonium chloride, stearyltrimonium bromide, behentrimonium methosulfate, hydrogenated tallow trimonium chloride, and fatty amines such as cetyldimethyl amine; stearyldimethylamine, behenyldimethyl amine, stearamidopropyl dimethylamine; behenamidopropyl dimethylamine, other cationic compounds and the like were found to generate significant synergistic thickening to the thickening composition. The cationic surfactant herein refers to a quaternary ammonium, and the cationizable surfactants refer to an alkylamine such as tertiary or secondary amine or primary amine or the like in its molecular structure, while having a relatively long alkyl carbon chain. Such alkylamine compound shows relatively strong cationic characteristics in an acidic system. The cationic or cationizable surfactant includes but not limited to quaternary surfactants, alkyl tertiary amine, alkylamide tertiary amine, acyl arginine esters, and acyl lysine esters and the like. The cationic surfactant can be expressed with a general Formula VI as follows:

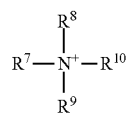

Formula VI

Wherein, R7=C8 to C28 alkyl, alkenyl, alkylamidopropyl or alkenylamidopropyl group; whereas R8, R9 and R10 are C1 to C5 alkyl, hydroxyalkyl, or carboxylic ester group or a polyoxyethylene group with a molar addition number of less than 10.

Typical quaternary surfactants include, but not limited to, cetyltrimethyl ammonium chloride, cetyltrimethyl ammonium bromide, stearyltrimethyl ammonium chloride, Behentrimonium Methosulfate, hydrogenated tallow trimonium chloride, etc.

Typical alkyl amines include, but not limited to, dimethyl cetylamine, dimethyl stearylamine, dimethyl behenyl propane diamine, etc.

Typical acyl arginine esters include, but not limited to, cocoacyl arginine ethyl ester and lauroyl arginine methyl ester.

Typical acyl lysine esters include, but not limited to, lauroyl lysine ethyl ester. Conditioning agents can be any skin or hair conditioning agents, including but not limited to polyquarternium-10, polyquarternium-7 and the like, silicones, quaternary ammoniums, long chain alkyl amines and the like. Other optional additives such as moisturizing agents, polymers, silicones, actives, chelating agents, salts, fragrances, preservatives and the like are not particularly limited and can be used either alone or in combination as needed.

The afore-mentioned self-thickening composition of the present invention can appropriately contain, besides the above-mentioned components, various further optional additives and other ingredients as component D for the general cosmetic formulations, OTC drugs and the like, to the extent that the effect of the present invention is not significantly impacted negatively. For example, optional one or more additives as component D may include further surfactants of all types (anionic surfactants such as acyl sarconsinate, acyl glycinate, acyl ananinate, acylmethyltaurate, sulfosuccinate, isothionate, alkylethercarboxylate, fatty acid salt, even alkylsulfate and alkylether sulfate, nonionic surfactants such as alkylglucosides, cationic surfactants such as cetrimonium chloride, steartrimonium chloride and the like, etc.), vegetable and synthetic oils such as olive oil, *camellia* oil, coconut oil, hydrogenated castor oil, beeswax, lanolin, squalene, Vaseline, silicone oil and the like, polymer thickeners such as carbomer, acrylates copolymer, xanthan gum, cellulose, guar gum, starch, carageenan, sodium alginate, bentonite, hectorite, and the like, conditioning agents include simple quaternary compounds such as Behentrimonium Methosulfate and the like as well as polymers such as polyquaternium-10, polyquaternium-7 and the like, preservatives, chelating agents, fragrances, colorants, dyes, pigments, actives such as sunscreens, antioxidant, anti-inflammatory agents, antimicrobial agent, antiperspirant, antidandruff agent, skin lighteners, moisturizers, vitamins, sensory agents for cooling or warming, pH adjusters and the like, according to the specific use and function of the cleansing compositions and the cosmetic compositions.

The weight percentages of component A and B in the afore-mentioned thickening composition of the present invention can both be in the range of about 0.5-60%, while that of component C can be in the range of 0.01-98%, and that of component D can be 0 to 20%. The weight percentage of component A is preferably 1.0-50%, more preferably 2-40%, still more preferably 3-30%, and further more preferably 3.5-20%, and particularly more preferably 4.0-10.0%; while the weight percentage of component B is preferably 1.0-50%, more preferably 1.5-40%; still more preferably 2.0-30%; and further preferably 2.5-20%, and particularly more preferably 3-10%. The weight ratio of component A to component B can be 95:5 to 5:95, preferably 10:1 to 1:10, and more preferably 5:1 to 1:5; and still more preferably 4:1-1:4; and further more preferably 3:1 to 1:3; and particularly more preferably 2:1 to 1:2. The weight percentage of water as component C may be 0.01-98%, and it can either come from the media of component A or B or both or be added separately, or a combination thereof. The weight percentage of optional one or more additives and other ingredients as component D can be 0 to 20%, preferably 0.05-15%, more preferably 0.1-10%, and still more preferably 0.2-8%, and further more preferably 0.5-5%, and particularly more preferably 1.0-3.0%.

The weight ratio of the total weight of components A, B and D to component C in the present invention is in general from about 2:98 to about 70:30. When the total weight of components A, B and D is less than 2%, the self-thickening effect becomes insufficient, while other problems such as solubility and precipitation may occur when the total weight of component A, B and D is more than 70%. A preferable ratio is from about 5:95 to about 60:40.

The total percentage of component A, B, C, and D shall be amounted to 100% by weight.

The preparation method of the thickening composition of the present invention includes the steps of (a) mixing component A and component B at a given ratio under agitation either with cold processing conditions or at mildly heated temperature, and then (b) adding water as Component C, and (c) adjusting pH with acid to a suitable pH within the range of 4.0-7.0 to achieve the desired viscosity to give the afore-mentioned self-thickening composition. In case that optional one or more additives and other ingredients as component D are used, the component D can be added either before or after component A, B and C are mixed with pH adjusted with cold processing or at an moderately elevated temperature.

The acid used to adjust the pH in the present invention can be either inorganic acid and/or organic acids. Either a single acid or a mixture of two or more acids can be used. Examples include but not limited to citric acid, lactic acid, acetic acid, oxalic acid, amino acid, hydrochloric acid, sulfuric acid, phosphoric acid, etc.

The thickening composition of the present invention has a viscosity of about 200 up to about 100,000 mPa·s or more in general. The viscosity of the thickening composition of the present invention is preferably 500-50,000 mPa·s, more preferably 1,000-30,000 mPa·s, still more preferably 3,000-20,000 mPa·s, further more preferably 4,000-18,000, and particularly more preferably 5,000-12,000 mPa·s. The viscosity can be easily controlled by changing the pH of the said thickening composition within the range of 4.0-7.0, the total weight percentage of component A and component B as well as the weight ratio of component A and component B.

As the thickening composition of the present invention can be made in a concentrated form of surfactant blend containing only components A and B, the viscosity of the concentrated blend can be very high within the pH range of 4.0-7.0 but very low with a pH above 7.0 to enable ease of handling and transportation. This is a great advantage compared to other thick surfactants which often cause problems in handling.

The thickening composition of the present invention can be used directly by incorporating it to the cosmetic compositions and cleansing compositions, and it may also be used as a concentrated blend which can be diluted to the desired active content level with the desired viscosity within pH 4.0-7.0. Additionally, it may also be used in the design of the cosmetic compositions and cleansing formulations using the principles of the self-thickening composition of the present invention to achieve thickening of the acyl glutamate cleansing formulation.

Although the use of the thickening composition of the present invention is not limited in any way, various cleansing compositions and cosmetic compositions can be provided. For example, cosmetic liquid soap, facial cleanser of all forms, cleansing cosmetics such as hair shampoos, baby shampoos, body wash, shower gels, feminine wash, and liquid hand cleansers may be used with the thickening composition. In addition, the afore-mentioned thickening composition of the present invention may also be used in home care product including but not limited to liquid dish detergent, laundry detergent, surface cleaners, fabric care, carpet care and the like. It may also be used in institutional and industrial applications, such as diary cleaners, hospital liquid hand cleansers, etc.

As indicated above, acyl glutamate surfactant is sulfate-free, mild, safe, green and most sustainable surfactant which is to become the next generation surfactant. It is a high-performing anionic surfactant with multi-functional properties of cleansing, emulsifying, penetrating and solubilizing. Cleansing compositions containing acyl glutamate at a significant level exhibit many advantages including safety, sustainability, mildness, non-irritating, excellent skin-feel, better color-retention for dyed hair, luxurious foam quality, similar pH to the skin, etc., and therefore it is highly desired to develop personal care cleansing formulations with acyl glutamate as the primary surfactant.

The acyl glutamate-containing cleansing formulations can be widely applicable to personal care cleansing such as shampoos, shower gels, hand cleansers, home care applications such as liquid dish detergent, laundry detergent, carpet, furniture and fabric care, institutional and industrial applications such as hospital hand cleansers and diary cleaners, etc.

In general, the desirable viscosity for cleansing compositions as commercial products ranges from 1000 to 10,000 mPa·s, while some may require a viscosity of 10,000 mPa·s or more. As mentioned above, acyl glutamate surfactant is intrinsically extremely difficult to thicken due to its unique molecular structure of the two relatively large water soluble carboxylic head groups, and the conventional thickening strategy, such as salt addition, does not work at all with acyl glutamate surfactant. When the active content of sodium cocoyl glutamate solution is as high as 25%, its viscosity is only about 10 mPa·s. Even combining with other co-surfactants such as amphoterics, conventional methods can only achieve very limited thickening effect with a viscosity of only about 200 mPa·s or less. The present invention is based on a surprising discovery that certain weight percentages of the acyl glutamate and the amphoteric surfactant and their weight ratio in combination with suitable pH ranges provide superior thickening effect.

Through a series of well-designed studies, the inventors of the present invention surprisingly discovered extremely efficient and cost-effective self-thickening compositions containing a suitable weight percentage of one or more acyl glutamate and its salt thereof as component A, and a suitable weight percentage of one or more amphoteric surfactant as component B, and an appropriate weight ratio of component A to component B, in a suitable pH range, to achieve a viscosity of about 200 to about 100,000 mPa·s, which can be 100 to 10,000 times higher than the conventional system.

The one or more amphoteric surfactants as component B in the present invention possess excellent stability in both acidic and alkaline pH conditions, and they are very mild and easily water soluble with great foam and foam stability and foam quality as well as system stability. The amphoteric surfactants also possess the property of cationic surfactants with certain level of anti-microbial activity, which can enhance the softness, conditioning and broad-spectrum anti-microbial activity of the cleansing composition.

When the term "about" is applied to a parameter, such as amount, pH, or temperature, unless stated otherwise, it indicates that the parameter can vary by at least 10%, preferably within 5%, and more preferably within 2%, and further more preferably within 1%. For example, a pH of "about 5" should be interpreted as falling into the range of 4.5 to 5.5, preferably 4.75 to 5.25, and more preferably 4.9 to 5.1, and further more preferably 4.95 to 5.05. As would be understood by a person skilled in the art, when a parameter is not critical, a number is often given only for illustration purpose, instead of being limiting.

The term "a," "an," or "the," as used herein, represents both singular and plural forms. In general, when either a singular or a plural form of a noun is used, it denotes both singular and plural forms of the noun.

EXAMPLES

The present invention is described in further detail in the following examples. These examples are provided for illustration purposes and shall not be construed as limiting. The materials that were used in the examples of the present invention of the thickening compositions and cleansing compositions as components A through D are listed in Table 1 below:

TABLE 1

Components A to D used in Examples of the present invention

| Component | Trade Name * or Generic Name | INCI Name | Active Content | Product Code & Salt Content |
|---|---|---|---|---|
| A | EVERSOFT ™ UCS-30S | Disodium Cocoyl glutamate | ~25% | UCS; 4-5% |
| A | EVERSOFT ™ ULS-30S | Sodium Lauroyl Glutamate | ~25% | ULS; 4-5% salt |
| B | EVERMILD ™ SB450 | Lauramidopropyl Hydroxysultaine | ~37% | SB450; ~7% salt, |
| B | EVERMILD ™ SB230 | Lauryl Hydroxysultaine | ~30% | SB230, ~7% salt |
| B | CAB | Cocoamidopropyl betaine | ~30% | CAB |
| B | BS-12 | Lauryl betaine | ~30% | BS-12, |
| B | EVERMILD ™ LG-30 | Sodium Lauroamphoacetate | ~32% | LG-30; 7~8% salt |
| D | EVERMINE ™ 18 | Stearamidopropyl dimethylamine | 100% | |
| D | EVERMINE ™ 22 | Behenamidopropyl Dimethylamine | 100% | |
| D | EVERGUARD ™ LAE | Ethyl lauroyl arginate HCl, | 100% | LAE |
| D | EVERGUARD ™ CAE | PCA Ethyl cocoyl arginate | 100% | CAE |
| D | EVERGUARD ™ LAE-20 | Ethyl lauroyl arginate HCl, Glycerin | 20% | LAE-20; |
| D | EVERGUARD ™ PE | Phenoxyethanol | 100% | PE |
| D | EVERPRO ™ LCG | Ethyl Lauroyl Arginate HCl, Caprylyl Glycol, Glycerin | 50% | LCG |
| D | EVERLIPID ™ EFA | Linoleamidopropyl PG-Dimonium Chloride Phosphate | ~30% (Solids) | EFA |
| D | EVERLIPID ™ PTC | Cocoamidopropyl PG-Dimonium Chloride Phosphate | ~40% (Solids) | PTC |
| D | 1631 | Cetyltrimonium chloride | 100% | 1631 |
| D | OLEESTER ™ ISL | Sodium Isostearyl Lactylate | 100% | ISL |
| D | EVERQUAT ™ MP | Myristamidopropyl PG-Dimonium Chloride Phosphate | ~50% | MP |

* Products with trade names of EVERSOFT ™, EVERMILD ™, EVERMINE ™, EVERPRO ™, EVERGUARD ™, EVERLIPID ™, EVERQUAT ™ etc. were all provided by SINO LION USA, which is the international marketer of these products. The products with generic names are obtained from the open market. The product codes for most SINO LION materials are provided in the last column of Table 1 and may be referred to elsewhere in this application for convenience.

Examples 1 to 12

Thickening compositions and cleansing compositions were prepared according to the formulations described in Table 2, and evaluated for viscosity thereof by the following method. The viscosity was measured at room temperature which varied within the range of 22 to 26° C. from time to time. A Brookfield Viscometer "DV2T extra" was employed with a speed of 20 rpm for 30 seconds and a spindle of No. 3 to 7, dependent upon the viscosity. The following experimental procedures were utilized for each formulation in Table 2: Component A, B and C and optionally component D were weighed accurately in the amounts according to Table 2, and mixed well until homogeneous with mild heating if necessary. The resultant composition was adjusted either with 50% citric acid or 30% NaOH to reach the desired pH and was let settle overnight for more than 12 hours and the viscosity was then measured the following day at room temperature. Table 2 shows the viscosity of the various thickening compositions with different weight percentages of component A and B as well as different weight ratio of component A to component B within the pH of 5.0-5.6.

As can be seen from the results of Examples 1 to 12 in Table 2, to obtain the thickening composition of the present invention containing N-acyl acidic acid and/or a salt thereof as component A, an amphoteric surfactant as component B, and water as component C, the appropriate weight ratio of component A to component B is essential with a suitable total active content within an appropriate pH range. For the thickening composition containing only EVERSOFT™ UCS-30S as component A and EVERMILD™ SB450 (lauramidopropyl hydroxysultaine) as component B, it was found that EVERSOFT™ UCS-30S (disodium cocoyl glutamate) can be thickened about 3 to about 700 times with a viscosity of about 30 to about 7260 mPa·s within the range of weight ratio of component A to component B between 0.34:1 and 3:1 with a total active content of 15% at a pH of about 5.2, while some representative data were shown in Examples 1 to 3 with Comparative Examples 1-2 in Table 2. As can be seen from the results of examples 1 to 3, the composition containing component A and B were thickened dramatically for up to about 1400 times compared to its individual component B. It was surprisingly discovered that in addition to the weight ratio and the total active content of component A and B, the appropriate pH is also essential for any thickening composition to achieve the desired viscosity. If the pH is not right, the composition cannot be thickened at all even if the weight ratio and total active content are appropriate.

For the thickening compositions and cleansing compositions containing EVERSOFT™ UCS-30S as component A, and EVERMILD™ LG-30 (sodium lauroamphoacetate) as component B in the compositions described in Table 2, Examples 4 to 6 were prepared along with the Comparative Examples 3 and 4, and the viscosity was evaluated for the different weight ratio of component A to component B with a suitable total active content of 15% (wt) at the pH-5.2.

As can be seen from the results in Examples 4 and 6 as well as those of comparative Example 1 in Table 2, the thickening composition of the present invention containing EVERSOFT™ UCS-30S as component A, and EVERMILD™ LG-30 as component B, and water as component C, and citric acid as pH adjuster as component D can be thickened up to about 1754 times compared to its individual component A. It was found that EVERSOFT™ UCS-30S (disodium cocoyl glutamate) can be thickened from about 3 to about 1754 times with a viscosity of 30 to 17540 mPa·s within the range of weight ratio of component A to B between 0.072:1 to 5.43:1, with the thickening effect reaching a maximum at the weight ratio of component A to B at about 0.34:1 while the thickening was not significant with the weight ratio of component A to B at more than about 5:1 as shown in Comparative Example 4 at the pH-5.2. It shall be mentioned that the right pH is essential for any thickening composition to achieve the desired viscosity.

It can also be seen in Table 2 that for further thickening compositions containing EVERSOFT™ UCS-30S (disodium cocoyl glutamate) as component A, and EVERMILD™ SB450 (lauramidopropyl hydroxysultaine) as component B, water as component C and citric acid as component D in the compositions described in Examples 7 to 9, the viscosity of the thickening composition can be increased drastically from about 1340 to about 3095 times compared with Comparative Example 1 with the viscosity of Example 9 reaching 30950 mPa·s. It is also clear from Table 2 that for further thickening compositions containing EVERSOFT™ UCS-30S (disodium cocoyl glutamate) as component A, both EVERMILD™ SB450 and EVERMILD™ LG-30 as component B, water as component C, and citric acid as the pH adjuster as well as other optional additives as component D in the compositions described in Examples 10 to 12, the viscosity of the thickening composition can be drastically increased as well with Example 10 reaching a viscosity of 78,200, about 7820 times increase compared with acyl glutamate solution in Comparative Example 1. It was also found that when the composition of example 12 was varied by changing the weight ratio of the two component B, i.e., the weight ratio of EVERMILD™ SB450 to EVERMILD™ LG-30 from 0 (only EVERMILD™ LG-30 as component B) to infinity (only EVERMILD™ SB450 as component B), while keeping the weight percentage of component A as well as the total weight percentage of the two component B the same as those in Example 12 with a pH at ~5.2, the viscosity of the various resultant compositions increased from 2,770 mPa·s to 10,360 mPa·s monotonically as the weight ratio of EVERMILD™ SB450 to EVERMILD™ LG-30 increased from 0 to 0.67, and then varied within a limited range of 10,360 to 13,480 mPa·s with the weight ratio of EVERMILD™ SB450 to EVERMILD™ LG-30 between 0.67 to 9.04 while reaching a maximum of 13,480 mPa·s with the weight ratio of EVERMILD™ SB450 to EVERMILD™ LG-30 at 4.02:1 as shown in Example 12, while the viscosity of the resultant composition with only EVERMILD™ SB450 as component B was 11,640 mPa·s. with a pH at 5.2. From the foregoing, it was found that higher viscosity can be achieved with higher active contents of the thickening composition, which was not possible with conventional techniques for cleansing compositions containing acyl glutamate surfactant.

Examples 13 to 20

Thickening composition as a surfactant blend and the application of the blend for cleansing compositions were prepared according to the formulations described in Table 3, and evaluated for viscosity thereof by the method described above. The composition in Example 13 was prepared by mixing component A and B and C and then the pH was adjusted to pH 5.22 and the resultant composition was let to settle overnight at room temperature and the viscosity was measured and provided in Table 3. Example 13 was used as a surfactant blend at a total active content of 25%, which was capable of self-thickening at the right pH with sufficient amount of active content when diluted with water at time of application with sufficient amount of active content when diluted with water at time of application. Comparative Example 5 was prepared by diluting the surfactant blend of the composition from Example 13 with water according to the weight ratio of 60:40 as shown in Table 3 and the resultant composition had a pH of 5.32 and a very low viscosity of 125 mPa·s. Example 14 was prepared in the same way as Comparative Example 5 except that the pH of the composition was adjusted to 5.20, and the resultant composition had a viscosity of 5,920 mPa·s., which clearly demonstrated that the pH of the composition is very critical on the thickening effect. The composition in Example 15 was prepared from that in Example 14 by adding the optional component D, e.g., EFA (short for "EVERLIPID™ EFA"-see Table 1 for more info) and the composition in Example 16 was prepared using the composition in Example 15 by adding a further component D-ISL (short for "OLEESTER ISL", see more info in Table 1) while the composition in Example 17 was prepared using the composition in Example 16 by adjustment of pH to 5.19. It was clear from Examples 14-17 that EFA had a positive impact to the viscosity of the thickening composition while ISL had a negative impact to the thickening composition. It is worth noting that the composition of Example 17 had a viscosity in the range of 10 (pH=5.73) to 2,480 (pH=5.39) mPa·s when the pH varied from 4.91 to 5.73 while the composition became cloudy when pH was at or below 5.0. Examples 18 to 21 were prepared in a similar fashion as to Examples 14 to 17, and the viscosity results of the resultant compositions were provided in Table 3. It can be seen from Example 18 to 19 in Table 3 that when 5% of APG (coco-glucoside, a non-ionic surfactant) was incorporated with 60% of the surfactant blend from Example 13 and water, the viscosity of the resultant composition was increased from 6,890 to 7,500 mPa·s without adjustment of pH at 5.15. When 1.0% EFA was added to the composition in Example 19 to produce Example 20, the viscosity was also increased from 7,500 mPa·s (Example 19) to 7,700 mPa·s (Example 20) without adjustment of pH and further increased to 8,080 mPa·s with adjustment of pH to 5.12 (Example 21), which demonstrated that EFA, an amphoteric conditioner, had a positive impact to the viscosity of the surfactant blend. It is clear from Example 18 to 21 that surfactant blend capable of self-thickening can be incorporated into cleansing formulations along with other additives such as non-ionic surfactant, conditioners and others with easy applicability and suitable viscosity, which were not possible with conventional techniques.

Comparative Examples 6 to 17

Additional thickening compositions and cleansing compositions containing one type of component A and two types of component B along with component C (water) and various optional component D were prepared according to the formulations described in Comparative Example 6 to 17 in Table 4. The experimental procedures used were similar as that described above. As can be seen from Table 4, most of the compositions did not thicken to a viscosity of more than 500 mPa·s with the given conditions except for Comparative Example 16, which further demonstrated that a combination of delicate conditions must be met in order to achieve a thickening composition.

TABLE 2

Example 13 to 15 & Comparative Example 1-4. Viscosity of the various thickening composition with different weight percentages of component A and B and different weight ratio of component A to B

| Component | | Ex. 1 | Ex. 2 | Ex. 3 | Comp. Ex. 1 | Comp. Ex. 2 | Comp. Ex. 3 | Ex. 4 | Ex. 5 |
|---|---|---|---|---|---|---|---|---|---|
| A | UCS in wt % (Active wt %) | 28.00 (7.09) | 34.00 (8.61) | 40.00 (10.1) | 60.00 (15.20) | — | — | 24.0 (6.08) | 34.0 (8.61) |
| B | SB450 in Wt % (Active wt %) | 21.27 (7.91) | 17.19 (6.39) | 13.1 (4.87) | — | 40.36 (15.00) | — | — | — |
| B | LG-30 in wt % (Active wt %) | — | — | — | — | — | 46.0 (15.0) | 27.4 (8.91) | 19.6 (6.39) |
| D | EFA | — | — | — | | | | | |
| D | ISL | — | — | — | | | | | |
| C | Deionized Water (wt %) | | | | To 100% | | | | |
| D | 50% Citric Acid | q.s. | q.s | q.s | q.s | q.s | q.s | q.s | q.s |
| | pH( as is) | 5.23 | 5.10 | 5.22 | 5.24 | 5.23 | 5.23 | 5.21 | 5.22 |
| | Viscosity mPa · s (22~26° C.) | 6760 | 8160 | 1880 | 10 | 5 | 1420 | 6370 | 4750 |
| | Appearance at RM TEMP (22~26° C.) | clear | clear | clear | clear | clear | clear | clear | clear |
| | Total Active( %) | 15.0 | 15.0 | 15.0 | 15.0 | 15.0 | 15.0 | 15.0 | 15.0 |
| | Weight ratio A to B | 0.90:1 | 1.35:1 | 2.08:1 | Infinity | 0 | 0 | 0.68:1 | 1.35:1 |

| Component | | Ex. 6 | Comp. Ex. 4 | Ex. 7 | Ex. 8 | Ex. 9 | Ex. 10 | Ex. 11 | Ex. 12 |
|---|---|---|---|---|---|---|---|---|---|
| A | UCS in wt % | 15.0 (3.80) | 50.0 (12.7) | 34.00 (8.61) | 34.00 (8.61) | 51.10 (13.20) | 40.0 (10.1) | 20.0 (5.07) | 34.0 (8.61) |

TABLE 2-continued

Example 13 to 15 & Comparative Example 1-4. Viscosity of the various thickening composition with different weight percentages of component A and B and different weight ratio of component A to B

| | Component | | | | | | | | |
|---|---|---|---|---|---|---|---|---|---|
| B | SB450 in Wt % (Active wt %) | — | — | 20.00 (7.43) | 60.00 (22.30) | 27.06 (9.80) | 30.0 (11.2) | 15.0 (5.61) | 16.0 (5.95) |
| B | LG-30 in wt % (Active wt %) | 34.4 (11.2) | 7.16 (2.33) | | | | 26.00 (8.32) | 13.0 (4.16) | 4.5 (1.48) |
| D | EFA | | | | | | 2.0 | 1.0 | — |
| D | ISL | | | | | | 1.6 | 0.8 | — |
| C | Deionized Water (wt %) | | | | To 100% | | | | |
| D | 50% Citric Acid | q.s | q.s | q.s | q.s | q.s | q.s | q.s | q.s |
| | pH (as is) | 5.09 | 5.26 | 5.21 | 5.26 | 5.21 | 5.57 | 5.34 | 5.17 |
| | Viscosity mPa·s (22~26° C.) | 17540 | 30 | 13400 | 27950 | 30950 | 78200 | 15120 | 13480 |
| | Appearance at RM TEMP (22~26° C.) | clear | clear | clear | clear | clear | clear | clear | clear |
| | Total Active (%) | 15.0 | 15.0 | 16.1 | 30.91 | 23.0 | 29.6 | 14.8 | 16.0 |
| | Weight ratio A to B | 0.34:1 | 5:43:1 | 1.16:1 | 0.39:1 | 1.29:1 | 0.52:1 | 0.52:1 | 1.16:1 |

TABLE 3

Example 13 to 21 & Comparative Example 5. Viscosity of the thickening blend with different component D

| | Component | Ex. 13 | Comp. Ex. 5 | Ex. 14 | Ex. 15 | Ex. 16 | Ex. 17 | Ex. 18 | Ex. 19 | Ex. 20 | Ex. 21 |
|---|---|---|---|---|---|---|---|---|---|---|---|
| A | UCS in wt % (Active wt %) | 56.67 (14.35) | (Comp. from Ex. 13): 60.0 | (Comp. from Ex. 13): 60.0 | (Comp. from Ex. 14): 99.0 | (Comp. from Ex. 15): 99.0 | (Comp. from Example 16): 99.0 | (Comp. from Ex. 13): 60.0 | (Comp. from Ex. 18): 95.0 | (Comp. from Ex. 19): 99.0 | (Comp. from Ex. 20): 100 |
| B | SB450 in Wt % (Active wt %) | 28.65 (10.65) | | | | | | | | | |
| D | EFA/ISL | — | — | — | 1.0 | /1.0 | — | — | — | 1.0 | — |
| D | APG0814 | — | — | — | — | — | — | — | 5.0 | — | — |
| C | Deionized Water (wt %) | | | | | To 100 | | | | | |
| D | 50% Citric Acid | q.s. | No adjustment | q.s | No adjustment | No adjustment | q.s | q.s | No adjustment | No adjustment | q.s. |
| | pH (as is) | 5.22 | 5.32 | 5.20 | 5.19 | 5.17 | 5.19 | 5.18 | 5.15 | 5.15 | 5.12 |
| | Viscosity mPa·s at RM Temp (22~26° C.) | 28200 (25.1° C.) | 125 (24.4° C.) | 5920 (24.4° C.) | 6860 (24.6° C.) | 1085 (23.7° C.) | 1130 (24.0° C.) | 6890 (24.4° C.) | 7500 (23.7° C.) | 7700 (24.4° C.) | 8080 (24.0° C.) |
| | Appearance at RM TEMP (22~26° C.) | clear | clear | clear | clear | clear | clear | clear | clear | clear | clear |
| | Total Active (%) | 25.0 | 15.0 | 15.0 | 15.0 | 15.0 | 15.0 | 15.0 | 17.5 | 17.5 | 17.5 |
| | Weight ratio A to B | 1.35:1 | 1.35:1 | 1.35:1 | 1.35:1 | 1.35:1 | 1.35:1 | 1.35:1 | 1.35:1 | 1.35:1 | 1.35:1 |

TABLE 4

Comparative Examples 6-17. Viscosity of the various compositions with different weight percentages of component A and B and different weight ratios of component A to B at various pH

| | Component | Comp. Ex. 6 | Comp. Ex. 7 | Comp. Ex. 8 | Comp. Ex. 9 | Comp. Ex. 10 | Comp. Ex. 11 | Comp. Ex. 12 | Comp. Ex. 13 | Comp. Ex. 14 | Comp. Ex. 15 | Comp. Ex. 16 | Comp. Ex. 17 |
|---|---|---|---|---|---|---|---|---|---|---|---|---|---|
| A | UCS/ULS* in wt % | 25.00 | 25.00 | 25.00 | /25.00 | /25.00 | /25.00 | /25.00 | /25.00 | /25.00 | 25.00 | 25.00 | 30.00 |
|   | (Active wt %) | (6.32) | (6.32) | (6.32) | (6.32) | (6.32) | (6.32) | (6.32) | (6.32) | (6.32) | (6.32) | (6.32) | (7.60) |
| B | SB450/SB230 in Wt % (Active wt %) | /10.00 (3.00) | /10.00 (3.00) | /10.00 (3.00) | — | /10.00 (3.00 | — | — | — | — | /10.00 (3.00) | /10.00 (3.00) | 18.00 (6.70) |
| B | LG-30/CAB in wt % (Active wt %) | 5.00 (1.6) | 5.00 (1.6) | 5.00 (1.6) | 5.00 (1.6) /10.0 (3.0) | 5.00 (1.6) | 5.00 (1.6) /10.0 (3.0) | 5.00 (1.6) /10.0 (3.0) | 5.00 (1.6) /10.0 (3.0) | 5.00 (1.6) /10.0 (3.0) | 5.00 (1.6) | 5.00 (1.6) | 10.00 (3.20) |
| D | EFA/MP//Na2EDTA | 2.00 | — | — | — | — | 2.00 | /2.00 | — | — | /2.00 | — | //0.05 |
| D | Evermine ™ 18/22 | — | 2.00 | — | — | — | — | /2.00 | 2.00 | — | /2.00 | — | |
| C | Deionized Water (wt %) | | | | | To 100 | | | | | | | |
| D | 50% Citric Acid | q.s. | q.s | q.s | q.s | q.s | q.s | q.s | q.s | q.s | q.s | q.s | q.s. |
|   | pH( as is) | 5.34 | 5.16 | 5.23 | 5.20 | 5.21 | 5.41 | 5.38 | 5.56 | 5.83 | 5.30 | 5.25 | 5.42 |
|   | Viscosity mPa·s( 22~26° C.) | ~1** | 420 | 50 | 50 | 35 | 700 | 850 | 400 | ~1** | 50 | 9200 | 410 |
|   | Appearance at RM TEMP (22~26° C.) | clear | clear | clear | clear | clear | semi-clear | clear | Opaque, milky | clear | Semi-clear | clear | clear |
|   | Total Active( %) | 10.9 | 10.9 | 10.9 | 10.9 | 10.9 | 10.9 | 10.9 | 10.9 | 10.9 | 10.9 | 10.9 | 17.5 |
|   | Weight ratio A to B | 1.37:1 | 1.37:1 | 1.37:1 | 1.37:1 | 1.37:1 | 1.37:1 | 1.37:1 | 1.37:1 | 1.37:1 | 1.37:1 | 1.34:1 | 0.77:1 |

*UCS/ULS: The number for UCS listed normally while that for ULS is listed with "/xxx" to different UCS from ULS. The same is true for SB450/SB30, LG-30/CAB; EFA/ISL//Na2EDTA; EVERMINE 18/22.
**"~1" recorded when no viscosity.

Thickening compositions and cleansing compositions of the present invention can provide a viscosity in the range of about 200 to about 100,000 mPa·s, preferably 500 to 50,000 mPa·s, more preferably 1,000 to 30,000 mPa·s, still more preferably 3,000 to 20,000 mPa·s, further more preferably 4,000 to 18,000 mPa·s, particularly more preferably 5,000 to 12,000 mPa·s. The following formulation examples are provided to illustrate the present invention, but not to limit its application scope. The compositions according to the present invention can be prepared by mixing each individual component with water while it is also possible to use the pre-mixtures of various ingredients, and many optional ingredients as component D can be added to create unlimited variations of all kinds of formulations.

Formulation Examples 1 to 11

Liquid cleansing compositions of the following formulations were prepared according to conventional methods. Suitable viscosity for personal care cleansing formulations can be obtained. Table 5 shows "Sulfate-Free" Glutamate Mild Body Wash Formulation Examples of 1 to 4, where all Formulation Examples demonstrated that EVERSOFT™ UCS-30S can be used as a primary surfactant along with other amphoteric surfactants such as EVERMILD™ SB450, CAB and/or EVERMILD™ LG-30 in sulfate-free systems and can achieve a desirable viscosity of about 4,000 to about 23,000 mPa·s within the pH of 5.0-5.7, which are well-suited for personal care cleansing formulations. It was found that EVERPRO™ LCG which contains the amino acid-derived preservative Ethyl Lauroyl Arginate HCl, a cationic compound, can provide additional synergistic effect of thickening in Formulation 1 and 4, which were also demonstrated in Formulation Examples 2 and 3, where Formulation 3 with 3.0% EVERPRO™ LCG had slightly higher viscosity than Formulation 2 without EVERPRO™ LCG.

Table 6 shows Formulations 5 to 7, which illustrate "Sulfate-Free" and polymer-free Glutamate Mild Hair Shampoo formulation examples that deliver good foaming and cleansing power with good compatibility with conditioning agents such as EVERLIPID™ EFA and OleEster™ ISL with sufficient viscosity up to 21,000 mPa·s at a pH of 5.22.

Table 7 presents "Sulfate-Free" Glutamate Cleansing Formulation Examples 8 to 11 with a viscosity range of 3,800 to 9,200 mPa·s within a pH of 5.01-5.25, which can be used as the basis for any personal care cleansing formulations such as body wash, hair shampoo, baby shampoo, hand cleanser, dish detergent, etc. Formulation 8 to 11 are clear viscous liquid, nevertheless, other additional ingredients may be added as needed to make them opaque, pearlescent, or colored formulations.

TABLE 5

"Sulfate-Free" Glutamate Mild Body Wash Formulation Examples 1 to 4

| Ingredient (% Wt) | Formulation 1 | Formulation 2 | Formulation 3 | Formulation 4 |
|---|---|---|---|---|
| Eversoft ™ UCS-30S | 25.00 | 30.00 | 30.00 | 30.00 |
| EVERMILD ™ SB 450 | — | 13.8 | 13.8 | — |
| CAB | — | — | — | 18.00 |
| EVERMILD ™ LG-30 | 25.00 | 10.00 | 10.00 | 10.00 |
| EVERLIPID ™ EFA/ Evermine ™ 18 | — | /1.38 | /1.38 | 1.0 |
| OleEster ™ ISL | — | — | — | 1.0 |
| Everpro ™ LCG | 1.5 | — | 3.0 | 3.0 |
| Na2EDTA | — | 0.05 | 0.05 | 0.05 |
| Fragrance | q.s. | — | — | — |
| Citric Acid (50%) | q.s. | q.s. | q.s | q.s. |
| Deionized Water | | To 100 | | |
| pH (~25° C.) (as is) | 5.60 | 5.35 | 5.55 | 5.50 |
| Viscosity mPa·s (~25° C.) | 3,900 | 20,000 | 23,000 | 16,600 |

TABLE 5-continued

"Sulfate-Free" Glutamate Mild Body
Wash Formulation Examples 1 to 4

| Ingredient (% Wt) | Formulation 1 | Formulation 2 | Formulation 3 | Formulation 4 |
|---|---|---|---|---|
| TOTAL SURFACTANT ACTIVE CONTENT | 14.3 | 16.0 | 16.0 | 16.1 |
| Appearance (RT, 25° C.) | clear viscous liquid | | | |

TABLE 6

"Sulfate-Free" Glutamate Mild Hair
Shampoo Formulation Examples 5 to 7

| Ingredient (% Wt) | Formulation 5 | Formulation 6 | Formulation 7 |
|---|---|---|---|
| Eversoft ™ UCS-30S | 20.0 | 30.0 | 30.0 |
| EVERMILD ™ SB 450 | 15.0 | 17.2 | — |
| CAB | — | — | 18.0 |
| EVERMILD ™ LG-30 | 13.0 | 10.4 | 10 |
| EVERLIPID ™ EFA | 1.0 | 0.80 | 0.8 |
| OleEster ™ ISL | 0.8 | 0.50 | 0.5 |
| EVERGUARD ™ LAE-20 | — | 0.40 | — |
| Everpro ™ LCG | — | 1.50 | 1.50 |
| EDTA-2Na | — | 0.05 | 0.05 |
| Fragrance | — | 0.10 | 0.10 |
| Citric Acid (50%) | | q.s | |
| Deionized Water | | To 100 | |
| pH (~25° C.) | 5.22 (as is) | 5.5 (as is) | 5.68 (10% Soln) |
| Viscosity mPa · s (22~26° C.) | 21,000 | 10,000 | 14,400 |
| Total Surfactant Active Content | 14.7 | 17.2 | 16.1 |
| Appearance (RT, 25° C.) | Slight yellowish clear viscous liquid | | |

TABLE 7

"Sulfate-Free" Glutamate Cleansing Formulation Examples 8 to 11

| Ingredient (% Wt) | Formulation 8 | Formulation 9 | Formulation 10 | Formulation 11 |
|---|---|---|---|---|
| Eversoft ™ UCS-30S | — | 25 | — | 25 |
| Eversoft ™ ULS-30S | — | — | 25 | — |
| Eversoft ™ ULK-30K | 25 | — | — | — |
| EVERMILD ™ SB 450 | — | — | — | 20 |
| EVERMILD ™ SB 230 | — | 10 | — | — |
| EVERMILD ™ LG-30 | — | 5 | — | — |
| CAB | 20 | — | 20 | — |
| EVERMINE ™ 22 | — | 2.00 | — | 1.0 |
| EVERGUARD ™ LAE | 0.3 | — | — | — |
| EVERGUARD ™ CAE | — | — | 0.3 | — |
| Citric Acid (50%) | q.s. | q.s. | q.s. | q.s. |
| Deionized Water | | To 100 | | |
| pH (~25° C.) | 5.20 | 5.25 | 5.17 | 5.01 |
| Viscosity mPa · s (~25° C.) | 5,000 | 9,200 | 3,800 | 5,700 |
| TOTAL SURFACTANT ACTIVE CONTENT | 12.3 | 10.9 | 12.3 | 13.7 |
| Appearance (RT, 25° C.) | clear viscous liquid | | | |

INDUSTRIAL APPLICABILITY

The present invention is easily scalable to industrial scale by simply mixing one acyl glutamate and/or the salt thereof as component A with one or more amphoteric surfactant as component B and optionally water as component C and optionally one or more other ingredients as component D, with either cold processing or some heating dependent upon the particular formulation. When the weight ratio of component A to B is in a suitable range with a sufficient total active content, a thickening composition can be obtained within a particular pH range. In addition, a commercial industrial scale Glutamate surfactant blend with one or more amphoteric surfactants and optionally a limited amount of water as well as a premix of two or more amphoteric surfactants can be obtained as an easy-to-use and easy-to-thicken blend and can be commercially valuable for cleansing compositions and cosmetic and personal care applications for skin, hair and the like.

Although the present invention has been described in some detail to facilitate understanding, it will be apparent that certain changes and modifications may be practiced within the scope of the present invention. Accordingly, the embodiments or preferred embodiments described herein are to be considered as illustrative and not restrictive, and the invention is not to be limited to the details given herein, but may be modified within the scope and equivalents of the appended claims. All the patent or non-patent references cited herein are incorporated by reference.

What is claimed is:

1. A sulfate-free self-thickening composition consisting of the following components:
    A. an N-acyl glutamic acid, or a salt or composition thereof;
    B. an amphoteric surfactant selected from the group consisting of cocoamidopropyl betaine, coco betaine, lauramidopropyl betaine, lauryl betaine, cocoamidopropyl hydroxysultaine, lauramidopropyl hydroxysultaine, coco hydroxylsultaine, lauryl hydroxylsultaine, sodium lauramphoacetate, sodium cocoamphoacetate, and mixtures thereof, or a composition thereof;
    C. water;
    D. optionally one or more other ingredients selected from the group consisting of anionic surfactants, nonionic surfactants, cationic surfactants, cationizable surfactants, conditioning agents, silicones, moisturizing agents, polymers, actives, vitamins, sunscreens, chelating agents, salts, fragrances, preservatives, and mixtures thereof;
    wherein component C (water) can be added separately or alternatively along with any of components A, B, and/or D; and the composition has a pH in the range of about 4.0 to about 7.0 with a viscosity in the range of about 200 to about 100,000 mPa·s; wherein the component A is 0.5-60% by weight of the thickening composition, the component B is 0.5-60% by weight of the thickening composition; and the weight ratio of component A to component B is in the range of 95:5 to 5:95; and wherein the component D is 0-20% by weight of the thickening composition.

2. The sulfate-free self-thickening composition of claim 1, wherein the salt of the N-acyl glutamic acid is a sodium, potassium, ammonium, or triethanolamine (TEA) salt.

3. The sulfate-free self-thickening composition of claim 1, wherein the acyl group of the N-acyl glutamic acid derives from a fatty acid comprising a C8 to C22 carbon chain.

4. The sulfate-free self-thickening composition of claim 3, wherein the fatty acid is selected from the group consisting of caprylic acid, capric acid, lauric acid, myristic acid, stearic acid, palmitic acid, oleic acid, linoleic acid, behenic acid, coconut acid, palm fatty acid, hydrogenated beef tallow fatty acid, and mixtures thereof.

5. The sulfate-free self-thickening composition of claim 2, wherein the acyl glutamic acid is selected from the group consisting of cocoyl glutamic acid, lauryol glutamic acid, myristoyl glutamic acid, and mixtures thereof; and wherein the salt is any one of cocoyl glutamate, lauroyl glutamate, or myristoyl glutamate salts, or a mixture thereof, comprising a counter cation selected from the group consisting of sodium, potassium, triethanolamine, and mixtures thereof.

6. The sulfate-free self-thickening composition of claim 1, wherein the amphoteric surfactant of component B is selected from the group consisting of cocoamidopropyl betaine, lauryl betaine, lauramidopropyl hydroxysultaine, lauryl hydroxylsultaine, sodium lauramphoacetate, and mixtures thereof.

7. The sulfate-free self-thickening composition of claim 1, wherein the amphoteric surfactant of component B is lauramidopropyl hydroxysultaine, sodium lauramphoacetate, or a mixture thereof; and wherein the component A is sodium cocoyl glutamate, disodium cocoyl glutamate, sodium lauroyl glutamate, disodium lauroyl glutamate, or a mixture thereof.

8. The sulfate-free self-thickening composition of claim 1, wherein the anionic surfactants are selected from the group consisting of acyl glycinate, acyl sarconsinate, acyl ananinate, acylmethyl taurates, alkyl isethionates, alkylether carboxylate, alkylsulfosuccinates, fatty acid salt, and combinations thereof; the cationic surfactants are selected from the group consisting of quaternary surfactants such as cetrimonium halides, steartrimonium halides and mixtures thereof; and the cationizable surfactants are selected from the group consisting of stearamidopropyl dimethylamine, stearamidopropyl diethylamine, behenamidopropyl dimethyamine, behenamidopropyl diethyamine and mixtures thereof; and the non-ionic surfactants are selected from the group consisting of alkylglucosides.

9. The sulfate-free self-thickening composition of claim 1, wherein the weight percentage of component A or component B is 1.0-50% in active content.

10. The sulfate-free self-thickening composition of claim 9, which contains 1-30% by weight of component A.

11. The sulfate-free self-thickening composition of claim 9, which contains 1-30% by weight of component B.

12. The sulfate-free self-thickening composition of claim 1, wherein the weight percentage of water as component C is 0.01-98%.

13. The sulfate-free self-thickening composition of claim 1, wherein the weight percentage of the optional one or more additives and other ingredients as component D is 0.05-15% in active content.

14. The sulfate-free self-thickening composition of claim 1, wherein the pH is within 4.5-6.5.

15. The sulfate-free self-thickening composition of claim 1, wherein the weight ratio of component A to component B is in the range of 3:1 to 1:3.

16. A sulfate-free self-thickening composition consisting of an N-acyl glutamic acid (component A) and an amphoteric surfactant (component B) selected from the group consisting of cocoamidopropyl betaine, coco betaine, lauramidopropyl betaine, lauryl betaine, cocoamidopropyl hydroxysultaine, lauramidopropyl hydroxysultaine, coco hydroxylsultaine, lauryl hydroxylsultaine, sodium lauramphoacetate, sodium cocoamphoacetate, and mixtures thereof, the composition having a pH in the range of about 5.5-12.0 with a viscosity suitable for ease of transporting and handling, wherein the viscosity of the composition will increase to a desired higher level as needed when it is used in a formulation by dilution with water and adjustment of pH; wherein the component D is 0-20% by weight of the thickening composition.

17. A method for producing a composition of claim 1, comprising the steps of (a) mixing component A and component B in their suitable weight percentages optionally in aqueous media, (b) stirring the mixture until it becomes uniform, and (c) adjusting pH with an acid until a desired viscosity is obtained.

18. A method for producing the thickening composition of claim 16, comprising mixing component A and component B in a limited amount of water in a pH in the range of about 5.5-12.0 until it becomes uniform.

19. A cleansing composition comprising a composition of claim 1 for use in cosmetic or personal care, home care, or institutional and industrial use.

* * * * *